United States Patent
Wagner

[19]

[11] Patent Number: 5,991,932
[45] Date of Patent: Nov. 30, 1999

[54] FEMALE URINARY AID DEVICE AND METHOD OF USE THEREOF

[76] Inventor: Janis L. Wagner, 2324 W. Argyle, Chicago, Ill. 60625

[21] Appl. No.: 08/864,729

[22] Filed: Jun. 9, 1997

Related U.S. Application Data

[63] Continuation-in-part of application No. 08/690,235, Jul. 19, 1996, abandoned.

[51] Int. Cl.[6] .................................................. A47K 11/12
[52] U.S. Cl. ............................................. 4/144.4; 4/144.1
[58] Field of Search ................................... 4/144.1, 144.4

[56] References Cited

U.S. PATENT DOCUMENTS

| | | | |
|---|---|---|---|
| 2,878,486 | 3/1959 | Bartlett et al. | 4/144.4 |
| 4,108,222 | 8/1978 | Kaufman | 141/337 |
| 4,608,046 | 8/1986 | Towfigh | 4/144.3 X |
| 4,681,573 | 7/1987 | McGovern et al. | 4/144.3 X |
| 4,734,941 | 4/1988 | DeWitt et al. | 4/144.4 |
| 4,751,751 | 6/1988 | Reno | 4/144.4 |
| 4,756,029 | 7/1988 | Zieve et al. | 4/144.4 |
| 4,937,890 | 7/1990 | Tafur | 4/144.4 |
| 5,330,453 | 7/1994 | Cornellier | 4/144.2 X |

FOREIGN PATENT DOCUMENTS 158 602  10/1985  European Pat. Off. ................ 4/144.4

OTHER PUBLICATIONS

"Standup Comedy," advertising, one page, date unknown.
"New! For Women Only," advertising, one page, date unknown.
"Ladies, Avoid Nighttime Bathroom Trips," advertising, one page, date unknown.

Primary Examiner—Robert M. Fetsuga
Attorney, Agent, or Firm—Brinks Hofer Gilson & Lione

[57] ABSTRACT

A female urinary aid device that allows a woman to urinate from a standing position. The device is formed of a sheet of material that is substantially symmetrical about a central longitudinal fold line. Angular edges, the symmetry of the device and trough-like passageway are provided so that the device is adaptable to the particular user. In use, the device provides a trough-like passageway. Handles may also be provided with the device to facilitate use of the device by persons with impaired finger dexterity and/or strength.

46 Claims, 3 Drawing Sheets

FEMALE URINARY AID DEVICE AND METHOD OF USE THEREOF

This application is a continuation-in-part of U.S. Ser. No. 08/690,235 filed on Jul. 19, 1996, abandoned.

FIELD OF THE INVENTION

This invention relates to a female urinary aid device and particularly to a female urinary aid device that allows a female to urinate comfortably in a standing position.

Urinary aid devices are useful for many reasons. Unsanitary conditions may be encountered in public restrooms. In such a case a woman may want to avoid making any physical contact with the toilet receptacle. Physically challenged women may find using a public toilet, or even the toilet in their home, difficult. It is thus desirable to provide a device that allows a woman to urinate comfortably in a standing position.

Several approaches to allowing a woman to urinate from a standing position have been taken. U.S. Pat. No. 2,878,486 discloses a sanitary device in the form of an intricately folded lightweight paper funnel. To use the device the woman must unfold the device and spread her legs far enough apart so as not to crush the device. This may be challenging for physically challenged women or women with large thighs. In addition, only one end of the device is configured to fit the woman. Also, the device is disposable and not reusable.

Another device is in the form of a plastic funnel. To use the device a woman needs to spread her legs at least a few inches. As previously mentioned, this may be difficult for physically challenged women or women with large thighs.

U.S. Pat. No. 4,756,029 discloses a feminine urinary device that allows a woman to urinate in a standing position. The device has a flat, flexible pad with a hinged flap and expandable side walls. The user must hold the pad firmly in place and align an opening in the pad with the urethra. Without the proper alignment, the device will not work and the user will end up soiling her clothes. In addition, to use the device the user must bend, which again may be difficult or uncomfortable for women who are physically challenged. In addition, the length of the device requires the user to stand close to the toilet receptacle thereby increasing the chance of the user soiling her clothes. In addition, the device is disposable and can not be reused.

U.S. Pat. No. 4,751,751 discloses a disposable urinating funnel for females in the shape of a thin paper funnel. When folded the device has a wide upper body portion to cover the woman's vaginal area and a tapering narrow bottom opening spout. The device opens by the application of pressure at the fold line and side edges. As with some of the devices previously described, only one end of the device is configured to fit the woman.

It is thus desirable to provide a female urinary aid device that is adjustable to better fit the individual user. It is also desirable to provide a female urinary aid device that can be used by the user in an easier to use, more natural stance. It is also desirable to provide a female urinary aid device that is more sanitary and allows the user to stand back further from the toilet receptacle which reduces the risk of soiling ones clothes. It is also desirable to provide a female urinary aid device that can be either disposed of or reused. It is also desirable to provide a female urinary aid device that is easy to use for persons with impaired finger dexterity and/or strength.

SUMMARY OF THE INVENTION

According to a first aspect of the present invention there is provided a urinary aid device for use by a woman in a standing position. The device includes a sheet of material being foldable to define a substantially flat member and expansible to define a trough-like passageway in a partially unfolded position. The trough-like passageway is defined by a central longitudinal fold line and two symmetrical panels coupled along the central longitudinal fold line. Each of the two symmetrical panels is defined by an outer boundary having a perpendicular edge at each end of the central longitudinal fold line, a central edge parallel to the central longitudinal fold line located about halfway between the perpendicular edges and angular edges connecting an end of a perpendicular edge to an end of the central edge.

According to a second aspect of the present invention there is provided a urinary aid device for use by a woman in a standing position. The device includes a sheet of material being foldable to define a substantially flat member and expansible to define a trough-like passageway in a partially unfolded position. The trough-like passageway is defined by two symmetrical panels joined by a central longitudinal fold line. Each passageway of the two symmetrical panels has a first end and a second end opposite to the first end, the first and second ends being symmetrical and contoured to engage the female perineal area.

According to a third aspect of the present invention there is provided a method of allowing a woman to urinate in a standing position. The method includes the steps of providing a sheet of material being foldable to define a substantially flat member and expansible to define a trough-like passageway in a partially unfolded position. The trough-like passageway is defined by a central longitudinal fold line and two symmetrical panels coupled along the central longitudinal fold line. Each of the two symmetrical panels is defined by an outer boundary having a perpendicular edge at each end of the central longitudinal fold line, a central edge parallel to the central longitudinal fold line located about halfway between the perpendicular edges and angular edges connecting an end of a perpendicular edge to an end of the central edge. Next one end of the sheet of material which includes two angular edges forming a V shape is positioned between the legs of a female. The sheet of material is then unfolded to fit the individual anatomy and the central longitudinal fold line is directed at a receptacle.

According to a fourth aspect of the present invention there is provided a urinary aid device for use by a woman in a standing position. The device includes a sheet of material being foldable to define a substantially flat member and expansible to define a trough-like passageway in a partially unfolded position. The trough-like passageway is defined by a central longitudinal fold line and two symmetrical panels coupled along the central longitudinal fold line. The sheet of material has a boundary defined by an octagon in the unfolded position.

According to a fifth aspect of the present invention there is provided a method of allowing a woman to urinate in a standing position. The method includes the steps of providing a sheet of material being foldable to define a substantially flat member and expansible to define a trough-like passageway in a partially unfolded position. The trough-like passageway is defined by two symmetrical panels joined by a central longitudinal fold line. Each passageway of the two symmetrical panels has a first end and a second end opposite to the first end, the first and second ends being symmetrical and contoured to engage the female perineal area. Next, one end of the sheet of material which includes two angular edges forming a V shape is positioned between the legs of a female. The sheet of material is then unfolded to fit the individual anatomy and the central longitudinal fold line is directed at a receptacle.

The invention itself, together with further objects and attendant advantages, will best be understood by reference to the following detailed description, taken in conjunction with the accompanying drawings.

DETAILED DESCRIPTION OF THE PRESENTLY PREFERRED EMBODIMENTS

Figure 1:
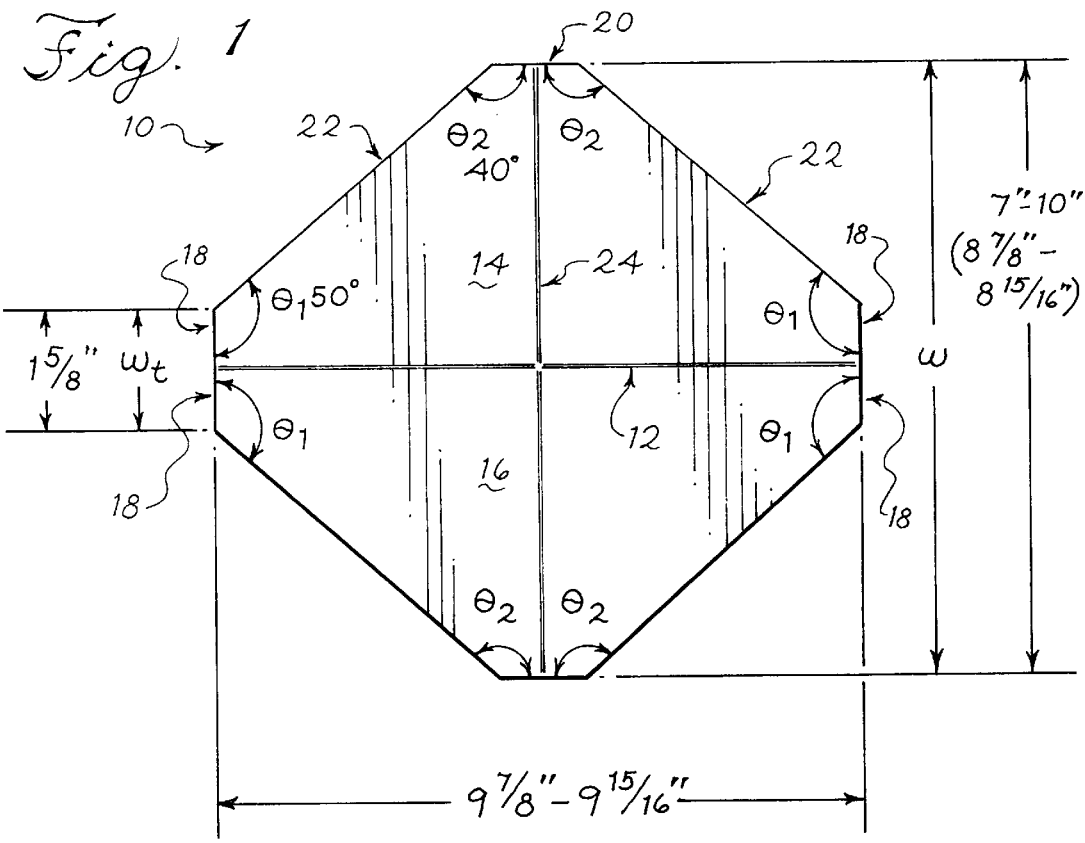
FIG. 1 is a top view of a female urinary aid device in an unfolded state according to a first preferred embodiment of the present invention.

FIG. 1 is a top view of a female urinary aid device 10 in an unfolded state according to a first preferred embodiment of the present invention. In a preferred embodiment, the device 10 has a central longitudinal fold line 12. The device 10 is substantially symmetrical about the central longitudinal fold line 12. More particularly, two symmetrical panels 14 and 16 are joined along the central longitudinal fold line 12. Each panel 14 and 16 is defined by a boundary having perpendicular edges 18 at the ends of the central longitudinal fold line 12, a central edge 20 parallel to the central longitudinal fold line 12 located about half way between the perpendicular edges 18 and angular edges 22 connecting one end of each perpendicular edge 18 to one end of a central edge 20. As illustrated, the device 10 when unfolded is octagonal in shape.

In a preferred embodiment, the length of the central longitudinal fold line 12 ranges from about 7 inches to about 12 inches. More preferably, the length of the central longitudinal fold line 12 ranges from about 9 and 7/8th inches to about 9 and 15/16th inches. The width w of the device preferably ranges from about 7 inches to about 10 inches. More preferably, the width w of the device 10 ranges from about 8 and 7/8th inches to about 8 and 15/16th inches. The angular edges 22 preferably form an angle $\theta_1$ of about 50° with respect to perpendicular edges 18 and an angle $\theta_2$ of 40° with respect to the central edges 20. Preferably the total width wt of the adjacent perpendicular edges 18 is about 1 and 5/8th inches.

In a preferred embodiment the device is formed of a sheet of paper-like material that is a highly calendared, dense, and non-coated paper, preferably having a caliper ranging from about 9 points to about 12 points such as Springhill Tag available from International Paper Company. The weight of the paper is preferably from about 100 pound to about 125 pound. Alternatively, a coated paperboard or a plastic may be used. Preferably the grain of the paper runs along the length of the device 10, i.e. in the same direction as the central longitudinal fold line 12.

A second fold line 24 perpendicular to the central longitudinal fold line 12 may be provided in the center of the device 10. This additional fold line 24 allows the device 10 to be folded for compact storage, for example, in a purse.

Figure 2:
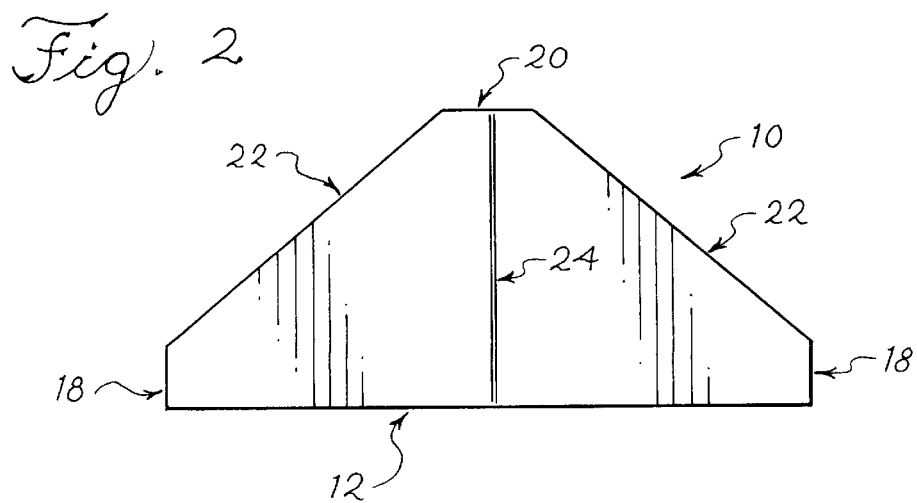
FIG. 2 is a side view of the female urinary aid device shown in FIG. 1 in its folded condition.

FIG. 2 is a side view of the female urinary aid device shown in FIG. 1 folded along center longitudinal fold line 12. It can be seen that the device 10 is substantially symmetrical about the central longitudinal fold line 12. In addition, if an additional fold line 24 is provided, the device 10 is also substantially symmetrical about fold line 24.

Figure 3:
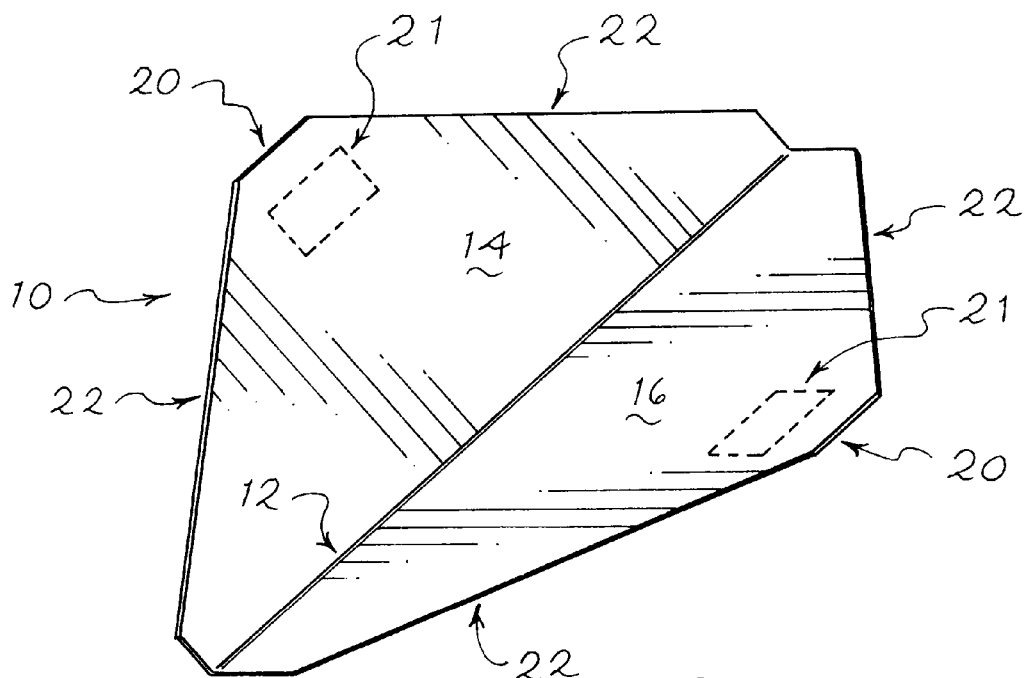
FIG. 3 is a perspective view of the female urinary aid device shown in FIGS. 1 and 2 in use.

FIG. 3 is a perspective view of the female urinary aid device shown in FIGS. 1 and 2 in a configuration in which it is neither fully unfolded as shown in FIG. 1 or fully folded as shown in FIG. 2 but rather a possible configuration when in use for example. The two symmetrical panels 14 and 16 and central longitudinal fold line 12 form a trough-like passageway. To use the device 10 the user positions one end of the device 10 which includes the perpendicular edges 18 between the legs of the user until at one end of the device the angular edges 22 cover at least a portion of the genital area. The user unfolds the device to fit the user's individual anatomy. The user holds the device in place with one or both hands at the widest point in the center of the device. The user stands naturally about 3 to about 6 inches from the toilet and aims the central longitudinal fold line at the receptacle. The symmetry, the angular edges and the trough-like passageway of the device makes it adjustable to the individual user.

The shape of the device makes it very easy to use. The angular edges, trough-like passageway and the symmetry and material combine to create a device that slides between a narrow space and can be widened and adjusted if necessary to accommodate the shape and needs of the particular user. Unlike some of the prior art devices discussed, there is no complex unfolding and/or shaping the device into funnels. Also the device can be used with one hand thereby accommodating a user with limited finger or arm dexterity. The device can slide back as far as necessary and adapts to each woman without her having to fit a fixed limited opening as is required by some of the known devices. The symmetry of the device allows the device to be used quickly at either end and its ease of fit provides better protection. Also, the shape of the device allows easy use because the user does not need to move her legs wide apart to adjust to a bulky device or to keep a flimsy device from collapsing between her legs. Not having to adapt to a wide stance requires less disturbance of the user's clothing. Also, the user can stand more naturally. The wide width of the device allows for ease of grip and no bending of the back or stretching arms or fingers. The long length of the device provides a better trajectory and allows the user to stand further away from the receptacle and ensures that the user's clothing will not be soiled. Also, the material used to form the device does not impose a time limit for its use unlike some of the known devices that begin to disintegrate after 30 to 60 seconds of urination. The device can be disposed of after one use or it may be wiped and reused.

On the exterior surface of the device 10 which is opposite of the surface shown in FIG. 1, handles 21 may be provided to assist the user in using the device. The handles 21 are schematically shown as dashed boxes for illustration purposes and in no way are intended to designate or limit the shape, position or location of the handles.

Figure 4:
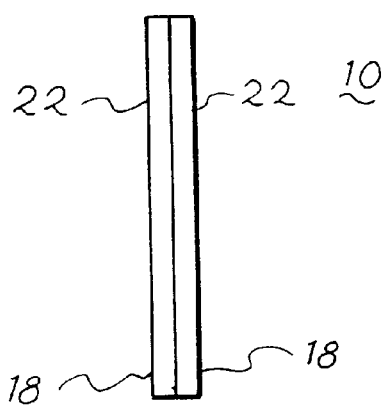
FIG. 4 is an end view of the female urinary aid device shown in FIG. 2 in its folded condition.
Figure 5:
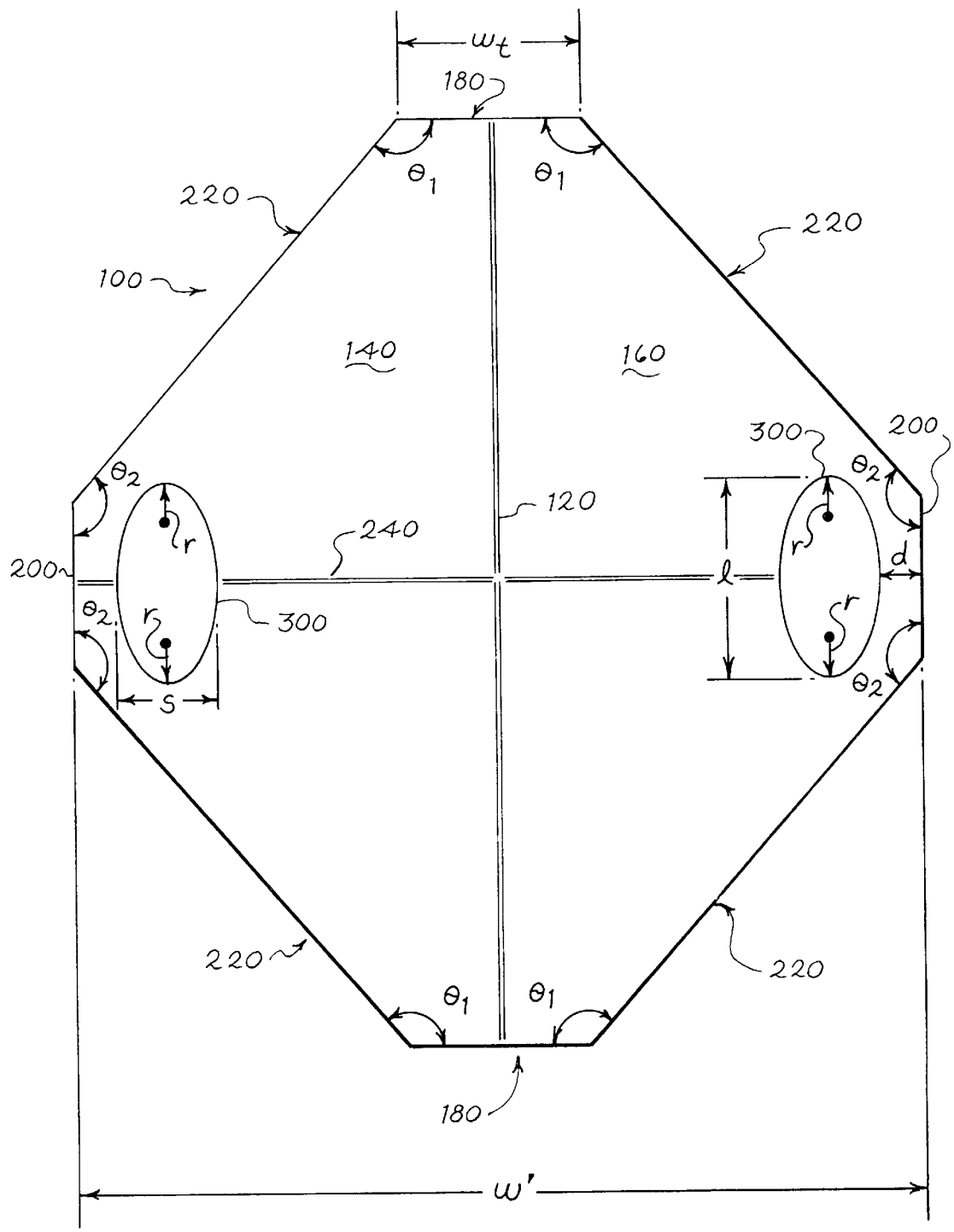
FIG. 5 is a top view of a female urinary aid device in an unfolded state according to a second preferred embodiment of the present invention.

FIG. 4 is a top view of a female urinary aid device 100 in an unfolded state according to a second preferred embodiment of the present invention. In a preferred embodiment, the device 100 has a central longitudinal fold line 120. The device 100 is substantially symmetrical about the central longitudinal fold line 120. More particularly, two symmetrical panels 140 and 160 are joined along the central longitudinal fold line 120. Each panel 140 and 160 is defined by a boundary having perpendicular edges 180 at the ends of the central longitudinal fold line 120, a central edge 200 parallel to the central longitudinal fold line 120 located about half way between the perpendicular edges 180 and angular edges 220 connecting one end of each perpendicular edge 180 to one end of a central edge 200. As illustrated, the device 100 when unfolded is octagonal in shape.

In a preferred embodiment, the length of the central longitudinal fold line 120 ranges from about 7 inches to about 12 inches. More preferably, the length of the central longitudinal fold line 120 is about 8.5 inches. The width w' of the device preferably ranges from about 7 inches to about 10 inches. More preferably, the width w' of the device 100 range is about 7.5 inches. The angular edges 220 preferably form an angle $\theta_1'$ of about 50° with respect to perpendicular edges 180 and an angle $\theta_2'$ of 40° with respect to the central edges 200. Preferably the total width $w_t'$ of the adjacent perpendicular edges 180 is about 1 and 5/8th inches. The central edges 200 preferably have a length of about 1.5 inches. The angular edges 220 preferably have a length of about 4 and 9/16th inches.

In a preferred embodiment a handle 300 is formed in each of the two symmetrical panels 140 and 160. The handles 300 are preferably in the form of cut-outs (i.e., material removed from the sheet of material forming the device) and most preferably are almost oval in shape. The cut-outs have a long axis extending in parallel with the central longitudinal axis 120. Preferably the long axis of the cut-outs ranges from about 1 inch to about 4 inches and more preferably is about 1 and 13/16th inches. The width S of the cut-outs 300, which is perpendicular to the central longitudinal fold line 120, preferably ranges from about 0.5 inches to about 2 inches and more preferably is about 23/32nd inches. The cut-outs are spaced preferably a distance d of about 7/16th inches from each central edge 200. The cut-outs have a radius r at each end of the long axis. Preferably the radius r ranges from about 1/16th of an inch to about 0.5 inches and more preferably is about 3/32nd of an inch.

A second fold line 240 perpendicular to the central longitudinal fold line 120 may be provided in the center of the device 100. The additional fold line 240 allows the device 100 to be folded for compact storage, for example, in a purse.

The device 100 shown in FIG. 4 has smaller dimensions than that shown in FIGS. 1–3 which makes the device 100 more convenient for travelers or those who in general want a more compact version. By providing handles 300 the device 100 is easier to grip and can be used by people with impaired finger dexterity and/or strength. For example, a person with arthritis may have painful and swollen finger joints and thus may be unable to grip or hold onto small objects even for a short time.

The handles 300 allow a person to slide one or a couple of fingers through each handle and let the device rest in place without having to grip the device to hold it in proper position. Otherwise the device 100 is used in the same manner as the device 10 shown in FIGS. 1–3.

While the preferred embodiment of the device 100 shows the handles 300 in the form of oval cut-outs of particular dimensions, other dimensions may be used and in fact cut-outs having other shapes may be used. In addition, the handles may be provided by features other than cut-outs.

In a preferred embodiment the device is formed of a sheet of paper-like material that is a highly calendared, dense, and non-coated paper, preferably having a caliper ranging from about 9 points to about 12 points such as Springhill Tag available from International Paper Company. The weight of the paper is preferably from about 100 pound to about 125 pound. Alternatively, a coated paperboard or a plastic may be used. Preferably the grain of the paper runs along the length of the device 10, 100, i.e. in the same direction as the central longitudinal fold line 12, 120.

It is to be understood that the forms of the invention described herewith are to be taken as preferred examples and that various changes in the shape, size and arrangement of parts may be resorted to, without departing from the spirit of the invention or scope of the claims.

What is claimed is:

1. A urinary aid device for use by a woman in a standing position, the device comprising:

a sheet of material being foldable to define a substantially flat member and expansible to define a trough-like passageway in a partially unfolded position, the trough-like passageway being defined by a central longitudinal fold line and two substantially symmetrical panels coupled along the central longitudinal fold line wherein each of the two symmetrical panels is defined by an outer boundary defined by a perpendicular edge at each end of the central longitudinal fold line, a central edge parallel to the central longitudinal fold line located about halfway between the perpendicular edges and angular edges connecting an end of a perpendicular edge to an end of the central edge.

2. A urinary aid device according to claim 1 wherein the angular edges of the two symmetrical panels form an angle ranging from about 49° to about 51° with reference to the perpendicular edges.

3. A urinary aid device according to claim 1 wherein the angular edges of the two symmetrical panels form an angle of 50° with reference to the perpendicular edges.

4. A urinary aid device according to claim 1 further comprising an additional fold line perpendicular to the central longitudinal fold line, the additional fold line further dividing the two symmetrical panels into four symmetrical panels.

5. A urinary aid device according to claim 1 wherein the material is paper treated with a polymer.

6. A urinary aid device according to claim 5 wherein the polymer is water soluble.

7. A urinary aid device according to claim 1 wherein the device has an interior surface and an exterior surface the device further comprising a handle located on the exterior surface of each of the two symmetrical panels of the device.

8. A urinary aid device according to claim 1 wherein the central longitudinal fold line has a length ranging from about 8.5 inches to about 12 inches.

9. A urinary aid device according to claim 8 wherein the central longitudinal fold line has a length of about 9 15/16th inches.

10. A urinary aid device according to claim 1 wherein the material is paper.

11. A urinary aid device according to claim 1 wherein the material is a flexible plastic.

12. A urinary aid device for use by a woman in a standing position, the device comprising:

a sheet of material being foldable to define a substantially flat member when the device is not in use and expansible to define a trough-like passageway in a partially unfolded configuration when the device is in use the trough-like passageway being defined by two substantially symmetrical panels joined by a central longitudinal fold line wherein the trough-like passageway has a first end and a second end opposite to the first end, the first and second ends being symmetrical and the two substantially symmetrically panels having side edges in parallel with the central longitudinal fold line that define an outer boundary of the device.

13. A urinary aid device according to claim 12 wherein the first and second ends have angular edges and end edges, wherein the end edges are perpendicular to the central longitudinal fold line and the angular edges couple an end edge to a side edge.

14. A urinary aid device according to claim 13 wherein the angular edges form an angle ranging from about 49° to about 51° with reference to the perpendicular edges.

15. A urinary aid device according to claim 12 wherein the material is paper.

16. A urinary aid device according to claim 12 wherein the material is a flexible plastic.

17. A method of allowing a woman to urinate in a standing position by providing a sheet of material foldable to define a substantially flat member when not in use and expansible to define a trough-like passageway in a partially unfolded configuration when the device is in use, the trough-like passageway being defined by a central longitudinal fold line and two substantially symmetrical panels coupled along the central longitudinal fold line, wherein each of the two symmetrical panels is defined by an outer boundary having a perpendicular edge at each end of the central longitudinal fold line, a central edge parallel to the central longitudinal fold line located about halfway between the perpendicular edges and angular edges connecting an end of a perpendicular edge to an end of the central edge wherein the central edge of each symmetrical panel defines an outer boundary of the device and is in contact with one another when the device is not in use and the edges are not in contact with the other central edge when the device is in its unfolded configuration, the method comprising the steps of:

positioning one end of a sheet of material which includes two angular edges forming a V shape between the legs of a female;

unfolding the sheet of material to fit the individual anatomy; and directing the central longitudinal fold line at a receptacle.

18. A urinary aid device for use by a woman in a standing position, the device comprising:

a sheet of material being foldable to define a substantially flat member when the device is not in use and expansible to define a trough-like passageway in a partially unfolded configuration when the device is in use, the trough-like passageway being defined by a central longitudinal fold line and two symmetrical panels coupled along the central longitudinal fold line wherein said sheet of material has a boundary defined by an octagon in its unfolded configuration, wherein said octagon is defined as a closed plane figure bounded by eight straight sides and has eight angles.

19. A urinary aid device according to claim 18 wherein the material is paper.

20. A urinary aid device according to claim 18 wherein the material is a flexible plastic.

21. A method of allowing a woman to urinate in a standing position by providing a sheet of material being foldable to define a substantially flat member when it is not in use and expansible to define a trough-like passageway in a partially unfolded configuration when the device is in use, the trough-like passageway being defined by two substantially symmetrical panels joined by a central longitudinal fold line wherein the trough-like passageway has a first end and a second end opposite to the first end, the first end and second end being symmetrical and the two substantialy symmetrically panels have side edges directly opposite of and parallel to the central longitudinal fold line, the method comprising the steps of:

positioning one end of the sheet of material which includes two angular edges forming a V shape between the legs of a female;

unfolding the sheet of material to fit the individual anatomy; and directing the central longitudinal fold line at a receptacle.

22. A urinary aid device according to claim 1 wherein the central longitudinal fold line has a length of about 8.5 inches.

23. A urinary aid device according to claim 22 wherein the device has a width of about 7.5 inches.

24. A urinary aid device according to claim 1 further comprising a handle formed in each symmetrical panel of the device.

25. A urinary aid device according to claim 24 wherein the handle is a cut-out made in each symmetrical panel of the device.

26. A urinary aid device according to claim 25 wherein the cut-out is oval in shape.

27. A urinary aid device according to claim 26 wherein the cut-out has a long axis extending in parallel with the central longitudinal fold line having a length ranging from about 1 to about 4 inches.

28. A urinary aid device according to claim 27 wherein the long axis has a length of $1^{13}/_{16}$ inches.

29. A urinary aid device according to claim 26 wherein the cut-out has a long axis extending in parallel with the central longitudinal fold line and a radius at each end of the long axis ranging from about $1/_{16}$th to about 0.5 inches.

30. A urinary aid device according to claim 29 wherein the radius is $3/_{32}$nd of an inch.

31. A urinary aid device according to claim 26 wherein the cut-out has a width ranging from about 0.5 to about 2 inches.

32. A urinary aid device according to claim 26 wherein the cut-out has a width of $23/_{32}$nd of an inch.

33. A urinary aid device according to claim 1 wherein the angular edges of the two symmetrical panels form an angle of about 40° with reference to the central edges.

34. A urinary aid device according to claim 26 wherein the cut-outs have a long axis extending parallel to the central longitudinal fold line.

35. A urinary aid device according to claim 12 further comprising a handle formed in each of the two symmetrical panels.

36. A urinary aid device according to claim 12 wherein the central longitudinal fold line has a length of about 8.5 inches.

37. A method according to claim 17 further comprising the steps of providing a handle in each of the two substantially symmetrical panels wherein the handles are cut-outs formed in each panel and further comprising the step of inserting at least one finger in each cut-out before positioning one end of the sheet of material between the legs of the female.

38. A urinary aid device according to claim 18 wherein the central longitudinal fold line has a length ranging from about 7 inches to about 12 inches.

39. A urinary aid device according to claim 38 wherein the central longitudinal fold line has a length of about $9^{15}/_{16}$th inches.

40. A urinary aid device according to claim 38 wherein the central longitudinal fold line has a length of about 8.5 inches.

41. A urinary aid device according to claim 18 further comprising a handle formed in each of the two symmetrical panels.

42. A urinary aid device according to claim 41 wherein each handle is a cut-out formed in each of the two symmetrical panels.

43. A urinary aid device according to claim 42 wherein each cut-out is oval in shape.

44. A urinary aid device according to claim 43 wherein each oval cut-out has a long axis extending parallel to the central longitudinal axis.

45. A urinary aid device for use by a woman in a standing position, the device comprising:

a sheet of material being foldable to define a substantially flat member and expansible to define a trough-like passageway in a partially unfolded position, the trough-like passageway being defined by a central longitudinal fold line and two substantially symmetrical panels coupled along the central longitudinal fold line wherein each of the two symmetrical panels is defined by an outer boundary defined by a perpendicular edge at each end of the central longitudinal fold line, a central edge parallel to the central longitudinal fold line located about halfway between the perpendicular edges and angular edges connecting an end of a perpendicular edge to an end of the central edge; and a handle formed in each symmetrical panel of the device.

46. A urinary aid device for use by a woman in a standing position, the device comprising:

a sheet of material being foldable to define a substantially flat member and expansible to define a trough-like passageway in a partially unfolded position, the trough-like passageway being defined by two substantially symmetrical panels joined by a central longitudinal fold line wherein each passageway of the two symmetrical panels has a first end and a second end opposite to the first end, the first and second ends being symmetrical; and a handle formed in each symmetrical panel of the device wherein said sheet of material has a boundary defined by an octagon, wherein said octagon is defined as a closed plane figure bounded by eight straight sides and has eight angles.

* * * * *

UNITED STATES PATENT AND TRADEMARK OFFICE
CERTIFICATE OF CORRECTION

PATENT NO. : 5,991,932
DATED : November 30, 1999
INVENTOR(S) : Janis L. Wagner

It is certified that error appears in the above-identified patent and that said Letters Patent is hereby corrected as shown below:

On the Title Page

In column 1, before line 1, under "U.S. PATENT DOCUMENTS", insert:

--Des. 356,865   3/1995   Ivie   D24/122--.

In column 1, after line 1, under "U.S. PATENT DOCUMENTS", insert:

--4,023,216   5/1977   Li   4/144,4--.

In the Claims

In claim 12, line 12, delete "symmetrically" and substitute --symmetrical-- in its place.

In claim 21, lines 10-11, delete "symmetrically" and substitute --symmetrical-- in its place.

Signed and Sealed this

Twenty-second Day of May, 2001

Attest:

NICHOLAS P. GODICI

Attesting Officer

Acting Director of the United States Patent and Trademark Office